US012648965B2

(12) United States Patent
Zhang et al.

(10) Patent No.: US 12,648,965 B2
(45) Date of Patent: Jun. 9, 2026

(54) USE OF BOVINE SPLEEN PEPTIDE POWDER IN IMPROVING SLEEP, PREVENTING OR TREATING DEPRESSION, OR IMPROVING INTESTINAL FUNCTION

(71) Applicant: BEIJING NO. 1 BIO-TECHNOLOGY DEVELOPMENT CO., LTD., Beijing (CN)

(72) Inventors: Bowen Zhang, Beijing (CN); Xinyue Zheng, Beijing (CN); Yuan Cao, Beijing (CN)

(73) Assignee: BEIJING NO.1 BIO-TECHNOLOGY DEVELOPMENT CO., LTD., Beijing (CN)

( * ) Notice: Subject to any disclaimer, the term of this patent is extended or adjusted under 35 U.S.C. 154(b) by 0 days.

(21) Appl. No.: 19/063,611

(22) Filed: Feb. 26, 2025

(65) Prior Publication Data

US 2025/0213618 A1     Jul. 3, 2025

Related U.S. Application Data

(63) Continuation of application No. PCT/CN2023/136683, filed on Dec. 6, 2023.

(30) Foreign Application Priority Data

| | | |
|---|---|---|
| Dec. 8, 2022 | (CN) .......................... | 202211570333.9 |
| Dec. 8, 2022 | (CN) .......................... | 202211570537.2 |
| Dec. 8, 2022 | (CN) .......................... | 202211570539.1 |

(51) Int. Cl.

| | |
|---|---|
| *A61K 35/26* | (2015.01) |
| *A23L 33/18* | (2016.01) |
| *A61K 38/01* | (2006.01) |
| *A61K 38/17* | (2006.01) |
| *A61P 25/24* | (2006.01) |

(52) U.S. Cl.
CPC .............. *A61K 35/26* (2013.01); *A23L 33/18* (2016.08); *A61K 38/012* (2013.01); *A61K 38/1709* (2013.01); *A61P 25/24* (2018.01)

(58) Field of Classification Search
CPC .. A61K 35/26; A61K 38/012; A61K 38/1709; A23L 33/18; A61P 25/24
See application file for complete search history.

(56) References Cited

U.S. PATENT DOCUMENTS

| | | | |
|---|---|---|---|
| 2006/0234943 A1* | 10/2006 | Wong ...................... | A61P 31/12 530/329 |

FOREIGN PATENT DOCUMENTS

| | | | | |
|---|---|---|---|---|
| AU | 2012213218 B9 * | 2/2017 | ............. | A61K 31/12 |
| CN | 1765371 A | 5/2006 | | |

| | | | | | |
|---|---|---|---|---|---|
| CN | 1290862 C | * | 12/2006 | | |
| CN | 103892166 A | | 7/2014 | | |
| CN | 103989041 A | | 8/2014 | | |
| CN | 108271901 A | | 7/2018 | | |
| CN | 111150066 A | | 5/2020 | | |
| CN | 111172229 A | | 5/2020 | | |
| CN | 111375048 A | | 7/2020 | | |
| CN | 112007140 A | | 12/2020 | | |
| CN | 112741887 A | | 5/2021 | | |
| CN | 113584108 A | * | 11/2021 | | |
| CN | 113647556 A | | 11/2021 | | |
| CN | 113841897 A | | 12/2021 | | |
| CN | 115299543 A | | 11/2022 | | |
| CN | 115624187 A | | 1/2023 | | |
| CN | 115624614 A | | 1/2023 | | |
| CN | 115644455 A | | 1/2023 | | |
| JP | 2000247903 A | | 9/2000 | | |
| KR | 20200065713 A | | 6/2020 | | |
| KR | 20220122194 A | | 9/2022 | | |
| WO | WO-2004017754 A2 | * | 3/2004 | ............... | A23L 1/30 |
| WO | 2006126574 A1 | | 11/2006 | | |
| WO | 2022173328 A1 | | 8/2022 | | |

OTHER PUBLICATIONS

International Search Report in corresponding International Patent Application No. PCT/CN2023/136683, mailed Mar. 6, 2024, 5 pages, English Translation only.

Wang Junwei, Efficacy of Calf Spleen Extractive for Patients with Ovarian Epithelial Malignant Tumor Treated with Postoperative Chemotherapy and Its Effect on MMP-2 and CA125, The Practical Journal of Cancer, Nov. 2017, vol. 32, No. 11.

Fan Lei et al., Effects of Spleen Polypeptide Injection Adjuvant Therapy on T Lymphocyte and Immunologic Factors in Patients with Colorectal Carcinoma, Chin J Mod Appl Pharm, Apr. 2020, vol. 37 No.7.

Peng Shuangqing, Key technologies for drug safety evaluation, p. 778, Published Oct. 1, 2013.

Tang Mei et al., "Study on effect of calf spleen extractive on immune function of advanced liver cancer patients subjected to TACE surgery", Shaanxi Medical Journal, Nov. 2015, vol. 44, No. 11.

He Haiyan, "Effect of spleen polypeptide injection on immune function and inflammatory response of patients with acute exacerbation of chronic obstructive pulmonary disease", Shandong Medicine, 2018, vol. 58, No. 6.

European Patent Application No. 23899997.3 Search Report dated Sep. 24, 2025, 13 pages.

Korean Patent Application No. 20257008508 Notice of Allowance dated Mar. 6, 2026 with English translation, 5 pages.

(Continued)

*Primary Examiner* — Titilayo Moloye

(74) *Attorney, Agent, or Firm* — Cozen O'Connor

(57) ABSTRACT

Provided in the present invention is the use of bovine spleen peptide powder in the preparation of food for improving the sleep of subjects, relieving clinical depression of subjects or improving the intestinal functions of subjects. further provided in the present application is the use of bovine spleen peptide powder in preparation of drugs for preventing or treating the sleep disorders or clinical depression of subjects, or for improving intestinal functions of subjects.

18 Claims, 8 Drawing Sheets

(56)                    References Cited

OTHER PUBLICATIONS

Jahangard et al., "Diminished functional properties of T regulatory cells in major depressive disorder: The influence of selective serotonin reuptake inhibitor," Journal of Neuroimmunology, vol. 344, No. 577250, Jul. 15, 2020, 7 pages.

Li et al., "The Treg/Th17 Imbalance in Patients with Obstructive Sleep Apnoea Syndrome," Mediators of Inflammation, vol. 2012, No. 2012, Dec. 31, 2012, 11 pages.

Boschetti et al., "Gut Inflammation in Mice Triggers Proliferation and Function of Mucosal Foxp3+ Regulatory T Cells but Impairs Their Conversion from CD4 + T Cells," Journal of Crohn's and Colitis, Jun. 30, 2016, 13 pages.

Wixler et al., "Small spleen peptides prevent development of psoriatic arthritis via restoration of peripheral tolerance," Molecular Therapy, vol. 30, No. 1, Aug. 2021, 18 pages.

"Fecal impaction," The Wayback Machine, Wikipedia, Sep. 28, 2022, https://web.archive.org/web/20220928044747/https://en.wikipedia.org/wiki/Fecal_impaction, 6 pages.

* cited by examiner

Normal control group    Model control group    Melatonin 125 μg/mL

Bovine spleen peptide    Bovine spleen peptide    Bovine spleen peptide
powder 62.5 μg/mL        powder 125 μg/mL         powder 250 μg/mL Normal control group    Model control group    Melatonin 125 μg/mL Bovine spleen peptide    Bovine spleen peptide    Bovine spleen peptide
powder 62.5 μg/mL        powder 125 μg/mL         powder 250 μg/mL

USE OF BOVINE SPLEEN PEPTIDE POWDER IN IMPROVING SLEEP, PREVENTING OR TREATING DEPRESSION, OR IMPROVING INTESTINAL FUNCTION

CROSS-REFERENCE TO RELATED APPLICATIONS

This application claims priority to Chinese Patent Application Nos. 202211570537.2, 202211570333.9 and 202211570539.1 filed on Dec. 8, 2022, which are incorporated herein by reference in their entirety.

TECHNICAL FIELD

The present application relates generally to the fields of biomedicine and food, and in particular, to the use of bovine spleen peptide powder in the manufacture of a food product for improving sleep in a subject, alleviating clinical depression in a subject, or improving intestinal functions in a subject, or in the manufacture of a medicament for preventing or treating a sleep disorder or clinical depression in a subject, or for improving intestinal functions in a subject.

BACKGROUND

Sleep disorders refer to various functional disorders in the sleep-wakefulness process, including insomnia, excessive sleepiness, sleep disordered breathing, and sleep behavior disorders due to various causes. Primary clinical signs are abnormal amounts of sleep (excessive or insufficient) and narcoleptic abnormalities in sleep (sleepwalking, somniloquy, nightmare, night terror, bruxism, and involuntary beating of muscle or limb). Sleep disorders primarily result from long-term mental conflicts or excessive mental burdens, mental labors, long-term improper handling of balance between work and rest, post-morbid weakness and the like.

In the Guidelines for the Diagnosis and Treatment of Insomnia in China, 2017, insomnia, the most common sleep disorder in clinic, refers to a sleep disorder characterized by frequent and persistent difficulty in falling asleep and/or difficulty in maintaining sleep and resulting dissatisfactory feelings with sleep. Adults that meet diagnostic criteria for insomnia are up to 10%~15%, and insomnia tends to be chronic, with nearly half of the severe insomnia lasting more than 10 years. Insomnia can cause fatigue, uneasiness, general malaise, listlessness, slow response, headache, and inattention, and if insomnia becomes severe, it will lead to functional disorders such as schizophrenia and clinical depression, anxiety disorders, vegetative nerve dysfunction, and disorders in various systems (such as cardiovascular system, digestive system, and the like).

Currently, western medicine mainly offers treatment with pharmaceuticals, which can be divided into six types: ① benzodiazepines; ② antidepressants; ③ antihistamines; ④ barbiturates and non-barbiturates; ⑤ antipsychotics and other sedatives; and ⑥ melatonin. Benzodiazepines as the main pharmaceuticals have the main pharmacological effects of anxiety resistance, sedation, hypnosis, convulsion resistance and skeletal muscle relaxation, and the main pathways are to promote the release of inhibitory neurotransmitters such as gamma-aminobutyric acid (GABA) and glycine from inhibitory neurons in brain, and to inhibit the production and release of 5-HT, thereby producing an anti-anxiety effect. However, long-term and large-dose use of common benzodiazepines and non-benzodiazepines for sedation and hypnosis can lead to serious adverse effects, making patients susceptible to tolerance and dependence.

Traditional Chinese medicine offers conditioning and favors treatment by traditional Chinese medicine prescriptions, acupuncture and moxibustion, acupoint massage and the like, but has the disadvantages of being time consuming and slow effects.

Clinical depression is a common type of mental disorders, and is characterized by a combination of multiple unique symptoms with the main symptoms of persistent low mood, lack of interest, anhedonia, inattention, sleep disorders, fatigue, suicidal ideation, somatic dysfunction, and the like.

Currently, clinical depression has become a major disabling cause in the world. The annual economic burdens from clinical depression are in the front rank among those for clinical diseases, and depression therefore has become a serious public health issue, the professional Recommendations for Treatment and Management of Clinical Depression (2022) provides use of antidepressants as follows.

(1) First-line drugs recommended for monotherapy of clinical depression according to guidelines in China and other countries: ① 5-serotonin reuptake inhibitors (SSRIs); ② 5-serotonin and norepinephrine reuptake inhibitors (SNRIs); ③ norepinephrine and dopamine reuptake inhibitors (NDRIs); and ④ other antidepressants. Agomelatine is a representative of agonists of melatonin receptors MT1 and MT2, and antagonists of 5-serotonin receptor 5-HT2C.

(2) Combined Antidepressants: in the clinical treatment of clinical depression, use of a single drug tends to be less effective, especially in terms of improvement of anxiety symptoms, so it is common to clinically use antidepressants in combination. The regimen of venlafaxine combined with mirtazapine is widely used clinically, but this regimen always lacks high-level clinical evidences. In addition, drug combinations inevitably have the problems of high doses and drug interaction, and generally result in more adverse effects. As the actual therapeutic effects have not been determined yet, they are not recommended.

Bowel dysfunction refers to gastrointestinal dysfunction, and patients with gastrointestinal dysfunction often have constipation symptoms. The American Gastroenterological Association (AGA) and the American College of Gastroenterology (ACG) have issued evidence-based practical recommendations for drug treatment of adult CIC involving the use of various over the counter drugs (OTCs) and prescription drugs for the treatment of CIC, including commonly used ① fibers; ② osmotic laxatives; ③ stimulant laxatives; ④ secretagogues and ⑤ 5-HT4 receptor agonists, but their resulting abdominal distension and gastrointestinal flatulence, nausea and diarrhea are common dose-dependent side effects.

It is necessary to develop a natural food product (such as food for special medical purposes or a health-care food product) that is free of side effects, safe and mild, effective in improving sleep, alleviating clinical depression in a subject, or improving intestinal functions in a subject, to prevent or treat a sleep disorder or clinical depression in the subject, or to improve intestinal functions in the subject, so as to alleviate the patient's suffering.

Bovine spleen peptides are in bovine spleen peptide powder with small molecules obtained by generally using purely natural bovine spleens as the raw material, and by a process including fragmentation, sterilization, biological enzymolysis, inactivation of enzyme(s), purification, concentration, centrifugal spraying, and drying. Bovine spleen peptide powder has very high activities, can be easily absorbed by a human body, can act to relieve fatigue and enhance immunity, has an effect of dispelling the effects of alcohol and protecting liver, and can help to reduce blood lipids and blood pressure.

SUMMARY

In a first aspect, provided in the present application is the use of bovine spleen peptide powder in the manufacture of a food product for improving sleep in a subject, or in the manufacture of a medicament for preventing or treating a sleep disorder in a subject.

In some embodiments of the first aspect, the subject has a sleep disorder.

In some embodiments of the first aspect, the sleep disorder is selected from one or more of insomnia, sleep disordered breathing, central disorders of hypersomnolence, circadian rhythm sleep-wake disorders (CRSWD), parasomnia, and sleep movement disorders.

In some embodiments of the first aspect, the improving sleep in the subject or treating a sleep disorder in the subject comprises one or more of increasing sleep time of the subject, increasing sleep efficiency of the subject, shortening sleep latency of the subject, reducing the amount of wake after sleep onset of the subject, and shortening the time of wake after sleep onset of the subject.

In a second aspect, provided in the present application is the use of the bovine spleen peptide powder in the manufacture of a food product for alleviating clinical depression in a subject, or in the manufacture of a medicament for preventing or treating clinical depression in a subject.

In a third aspect, provided in the present application is the use of the bovine spleen peptide powder in the manufacture of a food product for improving intestinal functions in a subject, or in the manufacture of a medicament for improving intestinal functions in a subject.

In some embodiments of the third aspect, the improving intestinal functions of the subject comprises lubricating the intestinal tract, and/or preventing, ameliorating, or treating constipation.

In some embodiments of any one of the first to third aspects, the bovine spleen peptide powder is used at a concentration of no more than 250 μg/mL.

In some embodiments of any one of the first to third aspects, the bovine spleen peptide powder, or the bovine spleen peptide powder together with food excipients, is prepared into a food product.

In some embodiments of any one of the first to third aspects, the food product is food for special medical purposes.

In some embodiments of any one of the first to third aspects, the food product is a health-care food product.

In some embodiments of any one of the first to third aspects, the bovine spleen peptide powder is formulated with a pharmaceutically acceptable carrier into a pharmaceutically acceptable dosage form.

In some embodiments of any one of the first to third aspects, the medicament is administered orally, subcutaneously, intramuscularly, or intraperitoneally.

In some embodiments of any one of the first to third aspects, the subject is a vertebrate.

In some embodiments of any one of the first to third aspects, the subject is fish, a mammal, cyclostomata, an amphibian, a reptile, or an avian.

In some embodiments of any one of the first to third aspects, the subject is fish or a mammal.

In some embodiments of any one of the first to third aspects, the bovine spleen peptide powder is prepared by a process comprising at least one of the following steps:

fragmentizing and homogenizing a bovine spleen to obtain a spleen slurry;

freezing and thawing the spleen slurry;

performing solid-liquid separation on the frozen and thawed spleen slurry to collect a supernatant;

filtering the supernatant to obtain a bovine spleen extract;

sterilizing the bovine spleen extract; and drying the sterilized bovine spleen extract to obtain the bovine spleen peptide powder.

In some embodiments of any one of the first to third aspects, polypeptides in the bovine spleen peptide powder are present in an amount of 150-200 mg/g.

In some embodiments of any one of the first to third aspects, polypeptide molecules in the bovine spleen peptide powder have molecular weights of less than 17 KD.

In some embodiments of any one of the first to third aspects, amino acids in the bovine spleen peptide powder are present in an amount of 400-450 mg/g.

In a fourth aspect, provided in the present application is a method of improving sleep in a subject, comprising administering to the subject an effective amount of bovine spleen peptide powder.

In a fifth aspect, provided in the present application is a method of preventing or treating a sleep disorder in a subject, comprising administering to the subject an effective amount of the bovine spleen peptide powder.

In a sixth aspect, provided in the present application is a method of alleviating clinical depression in a subject, comprising administering to the subject an effective amount of the bovine spleen peptide powder.

in a seventh aspect, provided in the present application is a method of preventing or treating clinical depression in a subject, comprising administering to the subject an effective amount of the bovine spleen peptide powder.

In an eighth aspect, provided in the present application is a method of improving intestinal functions in a subject, comprising administering to the subject an effective amount of the bovine spleen peptide powder.

In a ninth aspect, provided in the present application is a method of preventing, ameliorating, or treating constipation in a subject, comprising administering to the subject an effective amount of the bovine spleen peptide powder.

DETAILED DESCRIPTION

Figure 1:
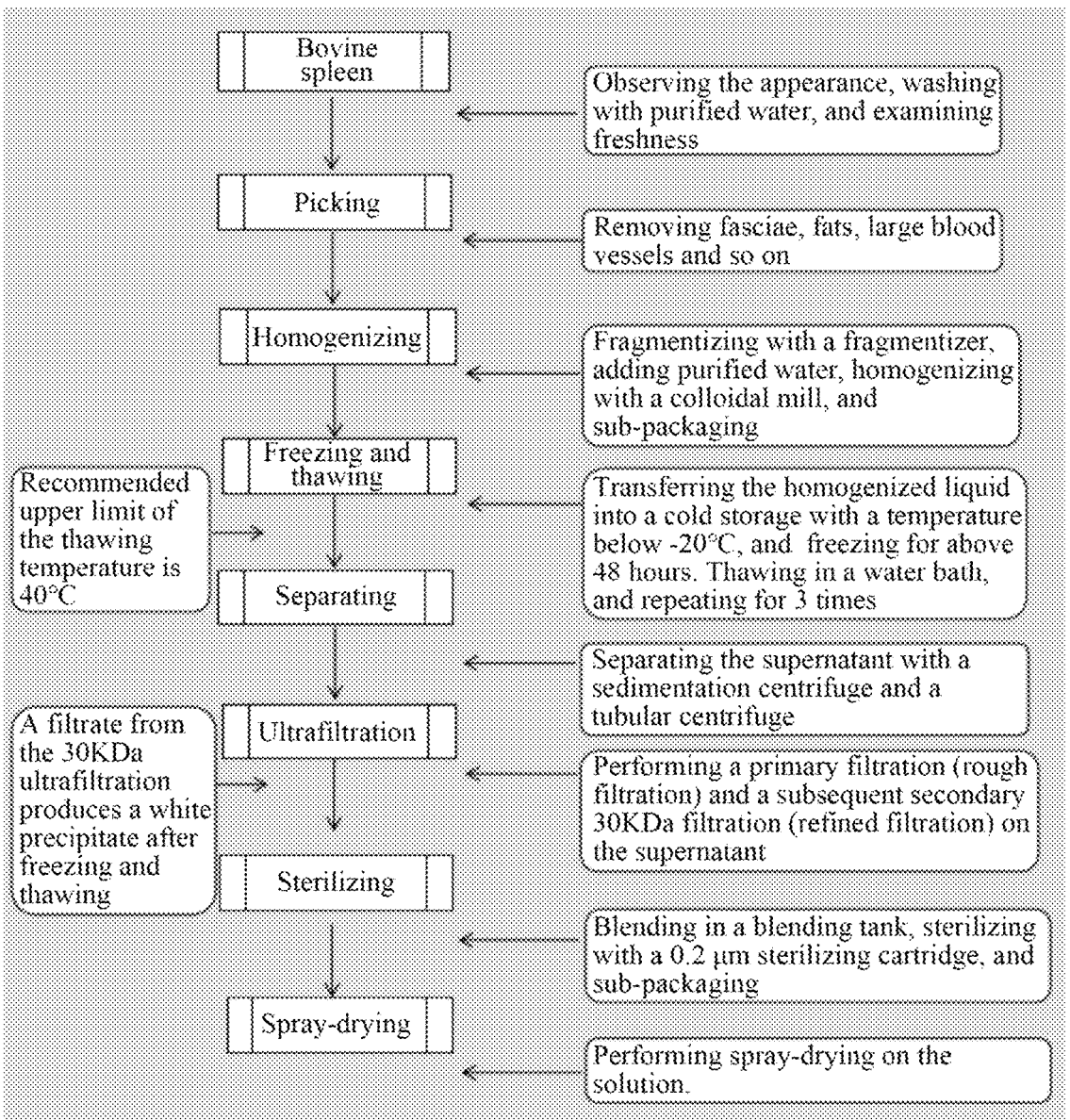
FIG. 1 shows a flow chart for the preparation of the bovine spleen peptide powder.
Figure 2:
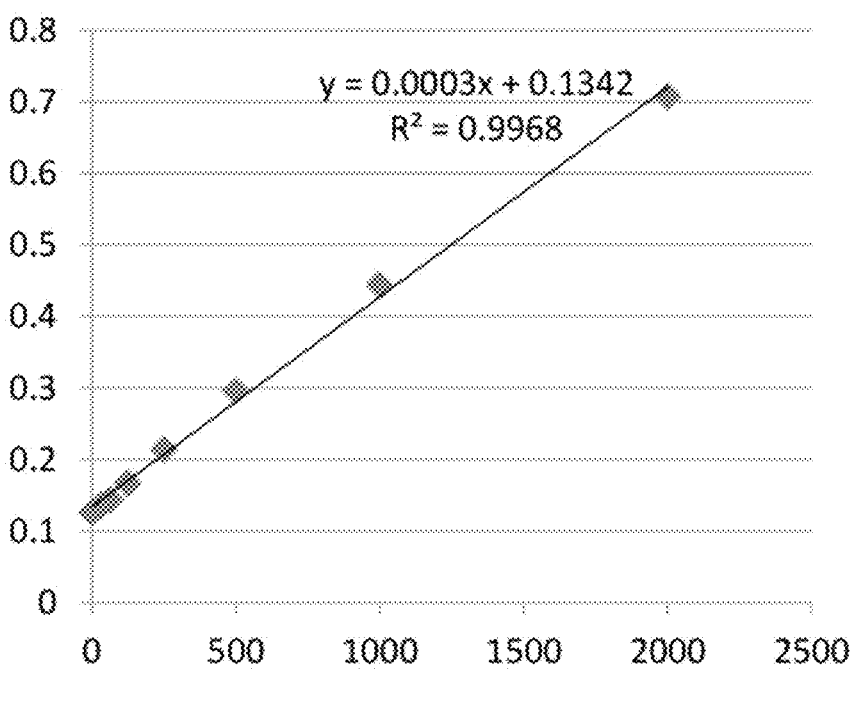
FIG. 2 shows a plot of a standard curve for the detection of polypeptide content in the bovine spleen peptide powder.

The inventors of the present application have found through experimentation that the bovine spleen peptide powder has the effects of facilitating improvement in sleep quality, resisting to clinical depression, or improving intestinal functions (e.g., lubricating the intestinal tract, or preventing, ameliorating, or treating constipation) in a subject. Thus, the bovine spleen peptide powder can be used for the preparation of a food product (e.g., food for special medical purposes or a health-care food product) for improving sleep in a subject, alleviating clinical depression (e.g., effectively relieving depressed mood as well as accompanying anxiety and tension) or improving intestinal functions in a subject, or for the preparation of a medicament for preventing or treating a sleep disorder or clinical depression in a subject, or for improving intestinal functions in a subject. Therefore, a new use of the bovine spleen peptide powder is developed.

Unless otherwise indicated, the practice of the present application employs technologies in the fields of molecular biology, microbiology, cell biology, biochemistry, and immunology which are conventional in the art.

Unless otherwise indicated, terms used in the present application have the meanings commonly appreciated by those skilled in the art.

Definitions

In the present application, a state in which zebrafish is in a speed of movement of greater than 20 mm/s is considered to be an awake state, a state in which the speed of movement is less than 4 mm/s is considered to be a sleep state, and a state in which the speed of movement is 4-20 mm/s corresponds to sleep latency.

As used herein, the term "food for special medical purposes" refers to a special food product that provides nutritional support to a population in a particular health condition. The term "health-care food product" refers to a food product having a health-care function. With respect to the definitions of the two food products, there are different provisions and requirements in different countries.

In China, food for special medical purposes (FSMP in short hereinafter) refers to a special category of food products which is developed for providing nutritional support to population with certain diseases or in particular health conditions, and has good effects in improving the therapeutic effect on diseases and the postoperative rehabilitation effect, improving the nutritional conditions in patients, enhancing the resistance of the body itself, and improving the overall health level of patients. The food for special medical purposes is a food product which is specially prepared to meet special needs for nutrients or meals of a population in a state of restricted eating, a digestion and absorption disorder, a metabolic disorder or a particular disease. Such products must be consumed alone or in conjunction with other food products under the guidance of a physician or a clinical dietitian.

In China, a health-care food product refers to a food product that has a health-care function or aims at supplementing nutrients such as vitamins and minerals. The health-care food is suitable for consumption by a particular population, has a function of regulating the body, is not intended to treat diseases, and does not cause any acute, subacute or chronic damages to the human body.

In the United States, the categories that are closest to the health-care food classification are dietary supplement and medical food, which are classified according to their functions. The dietary supplement is an oral product containing "dietary ingredients" used to supplement the diet, and the "dietary ingredients" include vitamins, minerals, herbal medicines, amino acids, and enzymes, organ tissues, glands, metabolites and the like. The medical food is defined in the Orphan Drugs Act (21 U.S.C. 360ee(b)(3)) Article 5(b)(3) and refers to a food product for oral use under the supervision of a physician, primarily for the specific dietary management of a disorder or physical condition.

In Australia, complementary medicines are equivalent to the health-care food products in China, and refer to therapeutic articles that contain, in whole or in part, one or more specific ingredients, each of which has a well-defined characteristic and a conventional mode of use, in particular the listed complementary medicines from the supplemental medicines.

In Japan, special foods are classified into three categories according to authentication modes, ingredients, functions, and labels: food for specified health uses, food with nutrient functions, and food with functional labels. The food for specified health uses (FOSHU) is defined as a food product that contains health-care functional ingredients having an effect on the physiological function of the human body and that contributes to the promotion of health or the alleviation of diseases. The food with nutrient functions refers to a food product used to supplement specific nutritional ingredients. The food with functional labels refers to a food product that is produced on a scientific basis, is not applied to patients, and contributes to maintaining or promoting health by the ingestion of "active ingredients" in such foods.

As used herein, the term "amount of wake after sleep onset" refers to the distance of movements during which the speed of movement is greater than 20 mm/s.

As used herein, the term "time of wake after sleep onset" refers to the time of movements during which the speed of movement is greater than 20 mm/s.

In a first aspect, provided in the present application is the use of the bovine spleen peptide powder in the manufacture of a food product for improving sleep in a subject.

In some embodiments of the first aspect, the improving sleep in the subject comprises one or more of increasing sleep time of the subject, increasing sleep efficiency of the subject, shortening sleep latency of the subject, reducing the amount of wake after sleep onset of the subject, and shortening the time of wake after sleep onset of the subject.

In a second aspect, provided in the present application is the use of the bovine spleen peptide powder in the manufacture of a food product for alleviating clinical depression in a subject.

In some embodiments of the second aspect, the food product may effectively alleviate depressed mood as well as accompanying anxiety and tension.

In a third aspect, provided in the present application is the use of the bovine spleen peptide powder in the manufacture of a food product for improving intestinal functions in a subject.

In some embodiments of any one of the first to third aspects, the bovine spleen peptide powder, or the bovine spleen peptide powder together with food excipients, is prepared into a food product.

In some embodiments of any one of the first to third aspects, the food excipient comprises a sweetener, an acidulant, and/or a preservative.

In some embodiments of any one of the first to third aspects, the sweetener is selected from one or more of sorbitol, fructose, glucose, lactose, mannitol, maltitol, and xylitol.

In some embodiments of any one of the first to third aspects, the acidulant is selected from one or more of citric acid, a lemon concentrate, tartaric acid, malic acid, lactic acid, and acetic acid.

In some embodiments of any one of the first to third aspects, the preservative is selected from one or more of benzoic acid, sodium benzoate, potassium sorbate, and sodium lactate.

In some embodiments of any one of the first to third aspects, the food product is food for special medical purposes.

In some embodiments of any one of the first to third aspects, the food product is a health-care food product.

In some embodiments of any one of the first to third aspects, the food product is a tablet, a powder, a granule, a medicinal tea, a hard capsule, a soft capsule, an oral liquid, a pill, a medicinal wine, an ointment, a beverage, pastry, liquid milks, biscuits, confectionery, a raw material extract, or a nutrient premix.

In a fourth aspect, provided in the present application is the use of the bovine spleen peptide powder in the manufacture of a medicament for preventing or treating a sleep disorder in a subject.

In some embodiments of the fourth aspect, the sleep disorder is selected from one or more of insomnia, sleep disordered breathing, central disorders of hypersomnolence, circadian rhythm sleep-wake disorders, parasomnia, and sleep movement disorders.

In some embodiments of the fourth aspect, the sleep disorder is insomnia.

In some embodiments of the fourth aspect, the sleep disorder in the subject comprises one or more of increasing sleep time of the subject, increasing sleep efficiency of the subject, shortening sleep latency of the subject, reducing the amount of wake after sleep onset of the subject, and shortening the time of wake after sleep onset of the subject.

In a fifth aspect, provided in the present application is the use of the bovine spleen peptide powder in the manufacture of a medicament for preventing or treating clinical depression in a subject.

In a sixth aspect, provided in the present application is the use of the bovine spleen peptide powder in the manufacture of a medicament for improving intestinal functions in a subject.

In some embodiments of any one of the fourth to sixth aspects, the bovine spleen peptide powder is formulated with a pharmaceutically acceptable carrier into a pharmaceutically acceptable dosage form.

In some embodiments of any one of the fourth to sixth aspects, the pharmaceutically acceptable carrier refers to a carrier that does not interfere with the biological activity of the active ingredient, including those conventionally used in the pharmaceutical field. The pharmaceutically acceptable carrier in the present application may be a solid or liquid, including a pharmaceutically acceptable excipient, a buffer, an emulsifier, a stabilizer, a preservative, a diluent, an encapsulant, a filler, and the like. For example, a pharmaceutically acceptable buffer further comprises a phosphate, an acetate, a citrate, a borate, a carbonate and the like. In some embodiments, the medicament of the present application for preventing or treating clinical depression in a subject may be prepared by any one of the methods well known in the pharmaceutical field. All of the methods include the step of combining the active ingredient of the present application with one or more pharmaceutically acceptable carriers. Generally, a composition is prepared by combining the active ingredient with a liquid carrier, a solid carrier, or both, followed by finalizing the dosage form of the resulting product as desired.

In some embodiments of any one of the fourth to sixth aspects, the bovine spleen peptide powder is formulated with a pharmaceutically acceptable carrier into an oral liquid, a capsule, a powder, a tablet, a granule, a pill, a syrup, a suppository or an injection.

In some embodiments of any one of the fourth to sixth aspects, the medicament is administered orally, subcutaneously, intramuscularly, or intraperitoneally.

In some specific embodiments of any one of the fourth to sixth aspects, the medicament is administered orally.

In some embodiments of any one of the above aspects, the bovine spleen peptide powder is used at a concentration of no more than 250 μg/mL, e.g., at a concentration of 1, 5, 10, 15, 20, 25, 30, 35, 40, 45, 50, 51, 52, 53, 54, 55, 56, 57, 58, 59, 60, 60.5, 61, 61.5, 62, 62.5, 63, 63.5, 64, 64.5, 65, 65.5, 66, 66.5, 67, 67.5, 68, 68.5, 69, 69.5, 70, 71, 72, 73, 74, 75, 76, 77, 78, 79, 80, 85, 90, 95, 100, 105, 110, 115, 120, 121, 122, 123, 124, 125, 126, 127, 128, 129, 130, 135, 140, 145, 150, 155, 160, 165, 170, 175, 180, 185, 190, 195, 200, 205, 210, 215, 220, 225, 230, 235, 240, 241, 242, 243, 244, 245, 246, 247, 248, 249 or 250 μg/mL, or a value or range between any two of these values.

In some embodiments of any one of the above aspects, the bovine spleen peptide powder is used at a concentration of 62.5-250 μg/mL, for example, at a concentration of 62.5, 63, 63.5, 64, 64.5, 65, 65.5, 66, 66.5, 67, 67.5, 68, 68.5, 69, 69.5, 70, 71, 72, 73, 74, 75, 76, 77, 78, 79, 80, 85, 90, 95, 100, 105, 110, 115, 120, 121, 122, 123, 124, 125, 126, 127, 128, 129, 130, 135, 140, 145, 150, 155, 160, 165, 170, 175, 180, 185, 190, 195, 200, 205, 210, 215, 220, 225, 230, 235, 240, 241, 242, 243, 244, 245, 246, 247, 248, 249 or 250 μg/mL, or a value or range between any two of the above values.

In some embodiments of any one of the above aspects, the bovine spleen peptide powder is used at a concentration of 62.5, 125, or 250 μg/mL.

In some embodiments of any one of the above aspects, the subject is a vertebrate.

In some embodiments of any one of the above aspects, the subject is fish, a mammal, cyclostomata, an amphibian, a reptile or an avian.

In some embodiments of any one of the above aspects, the subject is fish (e.g., zebrafish) or a mammal (e.g., human).

In some embodiments of the first or fourth aspect, the subject has a sleep disorder. In some embodiments, the sleep disorder is selected from one or more of insomnia, sleep disordered breathing, central disorders of hypersomnolence, circadian rhythm sleep-wake disorders, parasomnia, and sleep movement disorders.

In some embodiments of the second or fifth aspect, after consumption of the food product or administration of the medicament, the subject has elongated time of movements.

In some embodiments of the second or fifth aspect, after consumption of the food product or administration of the medicament, the subject has an increased distance of movements.

In some embodiments of the second or fifth aspect, after consumption of the food product or administration of the medicament, the subject has an increased time ratio of movements in bright field.

In some embodiments of the second or fifth aspect, after consumption of the food product or administration of the medicament, the subject has an increased distance of movements in bright field.

In some embodiments of the second or fifth aspect, the clinical depression comprises one or more of the following clinical symptoms:

1. affective symptoms: which are core symptoms of the depression disorder, manifested as persistent depressed mood, decreased interest, lack of energy;
2. physical symptoms: decreased appetite, insomnia, weight loss, decreased libido;
3. cognitive symptoms: inattention, decreased memory, slow thinking, with severe patients developing negative ideas, resulting in suicidal behaviors.

In some embodiments of the third or sixth aspect, the bovine spleen peptide powder is capable of increasing the number of goblet cells in the intestinal tract. The goblet cells are capable of synthesizing and secreting mucins, thereby lubricating the intestinal tract.

In some embodiments of the third or sixth aspect, the improving the intestinal function in the subject comprises lubricating the intestinal tract.

In some embodiments of the third or sixth aspect, the improving the intestinal functions in the subject comprises preventing, ameliorating or treating constipation.

In a seventh aspect, provided in the present application is a method of improving sleep in a subject, comprising administering to the subject an effective amount of the bovine spleen peptide powder.

In an eighth aspect, provided in the present application is a method of preventing or treating a sleep disorder in a subject, comprising administering to the subject an effective amount of the bovine spleen peptide powder.

In a ninth aspect, provided in the present application is a method of alleviating clinical depression in a subject, comprising administering to the subject an effective amount of the bovine spleen peptide powder.

in a tenth aspect, provided in the present application is a method of preventing or treating clinical depression in a subject, comprising administering to the subject an effective amount of the bovine spleen peptide powder.

In an eleventh aspect, provided in the present application is a method of improving intestinal functions in a subject, comprising administering to the subject an effective amount of the bovine spleen peptide powder.

In a twelfth aspect, provided in the present application is a method of preventing, ameliorating, or treating constipation in a subject, comprising administering to the subject an effective amount of the bovine spleen peptide powder.

In some embodiments of any one of the above aspects, the bovine spleen peptide powder is prepared by a process comprising at least one of the following steps:

fragmentizing and homogenizing a bovine spleen to obtain a spleen slurry;

freezing and thawing the spleen slurry;

performing solid-liquid separation on the frozen and thawed spleen slurry to collect a supernatant;

filtering the supernatant to obtain a bovine spleen extract;

sterilizing the bovine spleen extract; and drying the sterilized bovine spleen extract to obtain the bovine spleen peptide powder.

In some embodiments of any one of the foregoing aspects, the preparation of the bovine spleen peptide powder comprises the steps of selection of a bovine spleen, homogenization, freezing and thawing, solid-liquid separation, filtration (e.g., rough filtration and/or ultrafiltration) of the supernatant, sterilization, and spray-drying.

In some embodiments of any one of the above aspects, the polypeptides in the bovine spleen peptide powder are present in an amount of 150-200 mg/g, e.g., 150, 155, 160, 161, 161.1, 161.2, 161.3, 161.4, 161.5, 161.6, 161.7, 161.8, 161.9, 162, 163, 164, 165, 166, 167, 167.1, 167.2, 167.3, 167.4, 167.5, 167.6, 167.7, 167.8, 167.9, 170, 175, 180, 185, 190, 191, 192, 193, 194, 195, 195.1, 195.2, 195.3, 195.4, 195.5, 195.6, 195.7, 195.8, 195.9, 196, 197, 198, 199 or 200 mg/g, or a range between any two of the above values.

In some embodiments of any one of the above aspects, the amount of polypeptides in the bovine spleen peptide powder is 195.8 mg/g.

In some embodiments of any one of the above aspects, polypeptide molecules in the bovine spleen peptide powder have molecular weights of less than 17 KD.

In some embodiments of any one of the above aspects, amino acids in the bovine spleen peptide powder are present in an amount of 400-450 mg/g, e.g., 400, 401, 402, 403, 403.1, 403.2, 403.3, 403.4, 403.5, 403.6, 403.7, 403.8, 403.9, 404, 405, 406, 407, 407.1, 407.2, 407.3, 407.4, 407.5, 407.6, 407.8, 407.9, 408, 409, 410, 415, 420, 425, 430, 435, 440, 441, 442, 443, 444, 444.1, 444.2, 444.3, 444.4, 444.5, 444.6, 444.7, 444.8, 444.9, 445, 446, 447, 448, 449 or 450 mg/g, or a range between any two of the above values.

In some embodiments of any one of the above aspects, amino acids in the bovine spleen peptide powder are present in an amount of 444.5 mg/g.

In this specification and in the claims, the terms "including", "comprising" and "containing" mean "including, but not limited to", and do not intended to exclude other parts, additives, components or steps.

It is to be understood that features, characteristics, components, or steps described in a particular aspect, embodiment, or example of the present application may be applied to any other aspect, embodiment, or example described herein unless contradicted thereby.

The above disclosure generally describes the present application, and the following Examples are further illustrative of the application and should not be construed as limiting the application. The present application discloses the use of the bovine spleen peptide powder in the manufacture of a food product for improving sleep in a subject, alleviating clinical depression in a subject, or improving intestinal function in a subject, or in the manufacture of a medicament for preventing or treating a sleep disorder or clinical depression in a subject, or for improving intestinal function in a subject. those skilled in the art may refer to the contents herein to appropriately modify process parameters for implementation. In particular, it should be noted that all like alternatives and modifications will be apparent to those skilled in the art, and are considered to be included within the scope of the present invention. Those skilled in the art will be able to implement and apply the present invention by making alterations or suitable variations and combinations of the methods and applications described herein without departing from the disclosure, spirit and scope of the invention.

The present invention will be illustrated in details below in connection with the Examples so that those skilled in the art will better understand the technical solutions of the present invention.

EXAMPLES

Example 1 Preparation and Characterization of the Bovine Spleen Peptide Powder 1. Preparation of the Bovine Spleen Peptide Powder The method for preparing the bovine spleen peptide powder includes the following steps (a flow chart is shown in FIG. 1).

1) Fragmentizing and homogenizing. A fresh bovine spleen was washed, with fascia and trachea removed, and was then cut into pieces, homogenized in a homogenizer, added with purified water in a weight of 5 times of that of the fresh spleen homogenate, and stirred uniformly, so as to prepare a spleen slurry.

2) Freezing and thawing. The spleen slurry was frozen in a −20° C. cold storage for 48 hours or more, thawed in a water bath (upper limit of the thawing temperature was 40° C.), and repeatedly the freezing and thawing for three times.

3) Separating. The supernatant was obtained by separating using a sedimentation centrifuge and a tubular centrifuge.

4) Rough filtration. The supernatant obtained in step 3) was filtered through a filter membrane having a pore size of 50 μm to obtain a crude filtrate.

5) Ultrafiltration. The crude filtrate obtained in step 4) was subjected to ultrafiltration with an ultrafiltration membrane of 30 KDa, and the obtained ultrafiltrate was a bovine spleen extract.

6) Sterilizing. The extract was sterilized with a 0.2 μm sterilizing cartridge and was sub-packaged.

7) The sub-packaged solution of step 6) was spray-dried to obtain the bovine spleen peptide powder.

2. Characterization of the Bovine Spleen Peptide Powder 2.1 Detection of Polypeptide Content by BCA Assay Experimental instrument: UV spectrophotometer (Model: UV1800; Manufacturer: TOSOH).

Reagent for detection: BCA rapid-detection kit (Catalogue No.: A53225; Manufacturer: Thermo).

Sample preparation: 0.05 g of the bovine spleen peptide powder was sampled, dissolved in 10 mL of purified water and uniformly mixed for subsequent use.

The detection method includes the following steps.

1) The bovine serum albumin (BSA) standard (supplied in the kit) was serially diluted to 0.1, 0.2, 0.3, 0.4 and 0.5 mg/mL.

2) The preparation of BCA working solution: 100 mL of working solution A+2 mL working solution B in the kit was uniformly mixed.

3) The diluted standards and the sample to be tested were added to plates for microplate spectrophotometer (20 μL/well) respectively, and the BCA working solution was added at 200 μL, and incubated at 37° C. for 30 min;

4) The absorbance of each well was read at 562 nm, and a standard curve was plotted, so as to calculate the concentration of the sample to be tested.

The experimental results were shown in Table 2. The polypeptides in the bovine spleen peptide powder were present in an amount of 195.8 mg/g.

TABLE 1

| Detection results from the standard curve | | | | | | | |
|---|---|---|---|---|---|---|---|
| Concentration of the standard (μg/mL) | | | | | | | |
| 2000 | 1000 | 500 | 250 | 125 | 62.5 | 31.25 | 0 |
| Absorbance (OD value) 0.708 | 0.445 | 0.296 | 0.215 | 0.168 | 0.144 | 0.136 | 0.127 |

TABLE 2

| | | Detection results of the amount of polypeptides in the bovine spleen peptide powder sample | | | |
|---|---|---|---|---|---|
| Sample name | Absorbance (OD) | Concentration of polypeptide (mg/mL) | Total amount of polypeptides (mg) | Sample weight (g) | Polypeptide content (mg/g) |
| Bovine spleen peptide powder | 0.428 | 0.979 | 9.79 | 0.05 | 195.8 |

2.2 Detection of Molecular Weights of Polypeptides by SDS-PAGE Assay

Experimental instruments: a mini vertical electrophoresis apparatus (model number: BG-Power600; Manufacturer: Beijing Baijing Biotechnology Co., Ltd.), and a shaker for decolorization (Model: WD-9405D; Manufacturer: Beijing Liuyi Biotechnology Co., Ltd.)

Reagents for detection: a 12% Bis-Tris precast gel for electrophoresis (Model No.: MP0342BOX; Manufacturer: Thermo Scientific), an electrophoresis buffer (20×) (Model: NP0002; Manufacturer: Thermo Scientific), a protein staining solution (Model: 46-5034; Manufacturer: Thermo Scientific), a sample reducing agent (10×) (Model: NP0009; Manufacturer: Thermo Scientific), a sample buffer (Model: NP0007; Manufacturer: Thermo Scientific), and an electrophoretic protein molecular weight standard (Marker) (Model: 26619, Manufacturer: Thermo Scientific).

Sample preparation. 0.1 g of the bovine spleen peptide powder was sampled, dissolved in 10 mL of PBS and uniformly mixed for subsequent use.

The detection method includes the following steps.

1) 50 μL of the sample to be tested was added with 25 μL of the sample buffer, 10 μL of the sample reducing agent, and 15 μL of purified water, for a total volume of 100 μL.

2) The mixture obtained in step 1) was heated in boiling water for 3 minutes and then placed in a refrigerator at 4° C. for subsequent use;

3) The precast gels for electrophoresis was equilibrated to room temperature, opened, rinsed, placed in the pre-prepared electrophoresis buffer (1×), and loaded with the sample (10 μL of the sample to be tested, and 5 μL of the Marker). Subsequently, the electrophoresis apparatus was turned on, and electrophoresis was performed at a voltage of 120V until the bromophenol blue indicator was in the middle of the gel. The gel plate was removed and stained with the staining solution on the shaker for 60 minutes. The sample for quality control was bovine serum albumin (BSA) with a molecular weight of 66.4 KD.

4) At the end of the staining, decoloration was performed with purified water and the range of molecular weights was determined.

Figure 3:
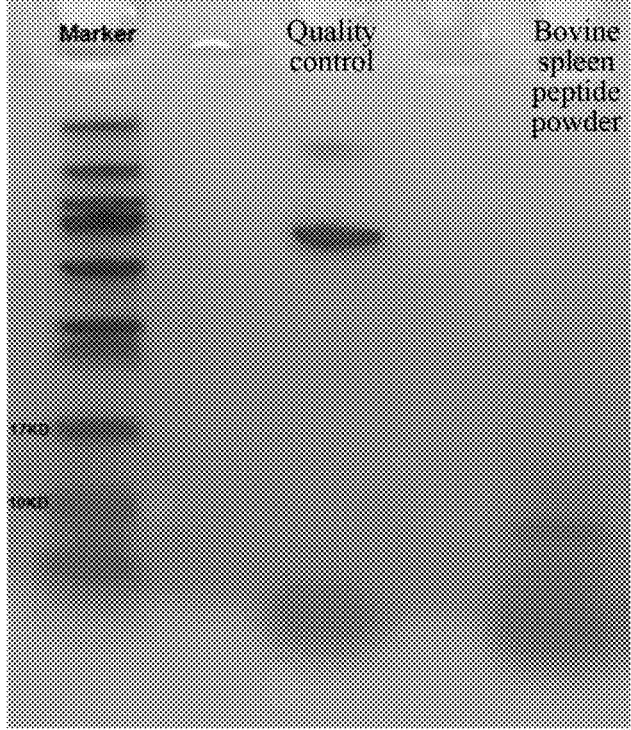
FIG. 3 shows the results of SDS-PAGE electrophoresis of the bovine spleen peptide powder.

As shown in FIG. 3, the molecular weights of the polypeptides in the bovine spleen peptide powder were mainly below 17 KD.

2.3 Detection of Contents of Amino Acids by HPLC Assay

Experimental instrument: high performance liquid chromatograph (Model: SPD-20A; Manufacturer: Shimadzu, Japan).

Reagents for detection: acetonitrile (Catalogue No.: 75-05-8; Batch No.: 203096; Manufacturer: Thermo Fisher Technology (China) Co., Ltd.), methanol (Catalogue No.: 67-56-1; Batch No.: 211775; Manufacturer: Thermo Fisher Technology (China) Co., Ltd.), and an amino acid assay kit (Catalogue No.: AJS-01; Manufacturer: Shimadzu, Japan).

Sample preparation. 0.03 g of the bovine spleen peptide powder was sampled, added with 5 mL of 0.1 mol/L hydrochloric acid, uniformly mixed, and filtered through a 0.45 μm filter membrane. 400 μL of the filtrate, 100 mL of 0.1 mol/L hydrochloric acid, and 50 μL of the internal standard substance were uniformly mixed until ready for use.

Detection Method:

Mobile phase: 9.0 g of disodium hydrogen phosphate dodecahydrate and 9.5 g of sodium tetraborate decahydrate were weighted, added with 2000 mL of water, with pH adjusted to 8.2 with hydrochloric acid, uniformly mixed, filtered through a 0.45 μm membrane and sonicated as mobile phase A. 450 mL of methanol, 450 mL of acetonitrile, and 100 mL of purified water were uniformly mixed, filtered through a 0.45 μm filter and sonicated as mobile phase B.

Figure 4:
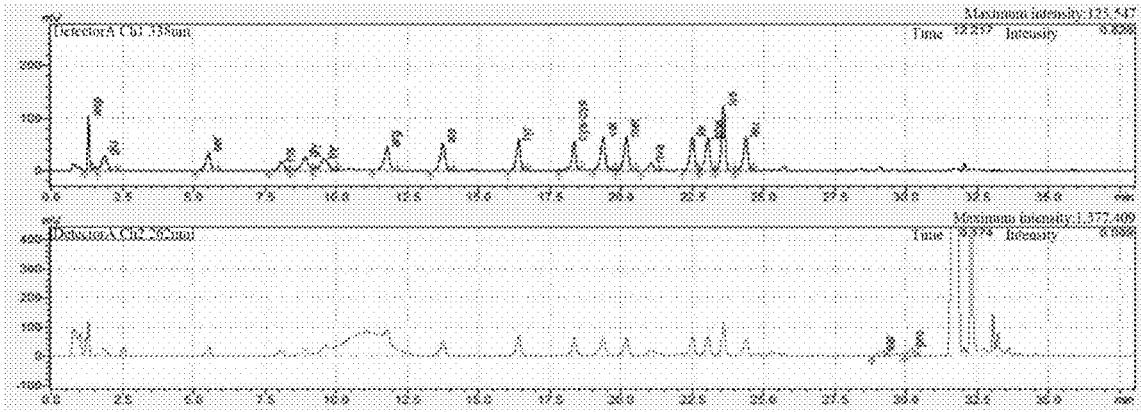
FIG. 4 shows the results of HPLC detection of amino acid standards.

Wavelength: 338 nm and 262 nm for UV detector;

Column temperature: 50° C.;

Chromatographic column: C18;

Flow rate: 1.0 mL/min;

Injection amount: 1 μL;

Sample processing: Derivatization 1) 1 μL of a standard mixture of 17 kinds of amino acids was accurately taken and injected into a liquid chromatography. A chromatogram was recorded. The experimental results were shown in FIG. 4.

2) 1 μL of the sample was accurately taken and injected into a liquid chromatographic column. A chromatograph was recorded.

Figure 5:
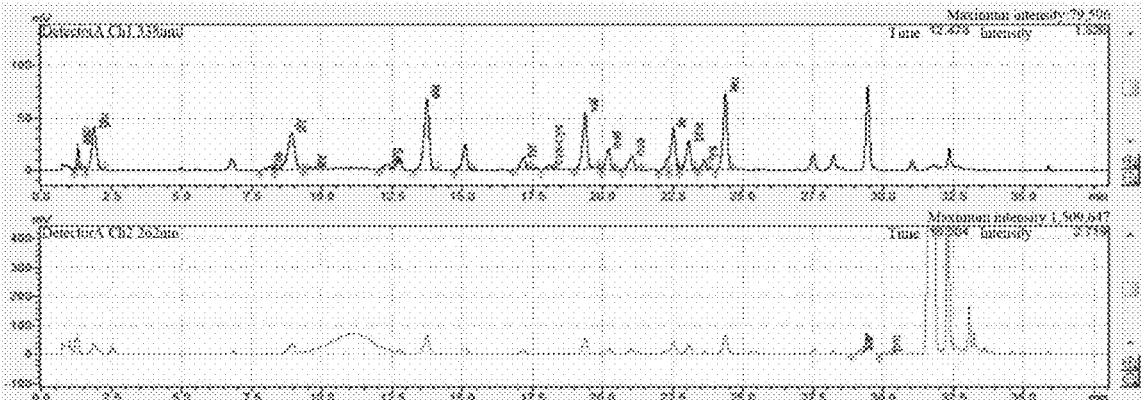
FIG. 5 shows the results of HPLC detection of amino acid contents in the bovine spleen peptide powder.

As shown in FIG. 5 and Table 3, the amino acids in the bovine spleen peptide powder were present in an amount of 444.5 mg/g.

TABLE 3

| Results of detection of amounts of amino acids in the bovine spleen peptide powder sample | | |
|---|---|---|
| Concentration of the standards (mg/mL) | Concentration of the sample (mg/mL) | The amount of the sample (mg/g) |
| 5.637 | 2.667 | 444.5 |

Example 2 Validation of Efficacy of the Bovine Spleen Peptide Powder in Improving Sleep 1. Materials for Detection 1.1 Information about Sample Preparation The bovine spleen peptide powder was prepared into a stock solution of 20.0 mg/mL with standard dilution water, sonicated and was ready for use.

Positive control: melatonin, which was a white powder from Shanghai Aladdin Biochemical Technology Co., Ltd., under batch number F1804064, was stored in a cool environment in dark. It was prepared with DMSO into a stock solution of 50.0 mg/mL and stored at −20° C.

1.2 Experimental Animals

The zebrafish, provided by the fish breeding center of Hangzhou Huante Biotechnology Co., Ltd., were all housed in fish water at 28° C. (water quality: 200 mg of instant sea salt per 1 L of reverse osmosis water, with a conductivity of 450-550 μS/cm; a pH of 6.5-8.5; a hardness of 50-100 mg/L CaCO₃), and the laboratory animal use license number was SYXK (Zhejiang) 2022-0004. The feeding management fulfilled the requirements of international AAALAC certification (certification number: 001458).

The wild-type zebrafish of AB line were propagated by the way of natural pairwise breeding. Zebrafish aged 5 days post-fertilization (5 dpf) were used for the maximum toleration concentration (MTC) measurement and evaluation of efficacy of the bovine spleen peptide powder for improving sleep.

1.3 Instruments, Consumables and Reagents

A dissecting microscope (SZX7, OLYMPUS, Japan); a CCD camera (VertA1, Shanghai Tusen Vision Technology Co., Ltd., China); a precision electronic balance (CP214, OHAUS, USA); a behavior analyzer (Zebra Lab 3.22.3.31, Viewpoint, France); 6-well plates (Nest Biotech, China); and 96-well plates (Nest Biotech, China).

Pentylenetetrazole (PTZ, batch number YH0171126, Shanghai Yihe Biotechnology Co., Ltd., China); and dimethyl sulfoxide (DMSO, batch No. BCCD8942, Sigma, Switzerland).

2. Detection Method 2.1 MTC Assay

The 5 dpf wild type zebrafish line AB were randomly selected and placed in a 6-well plate, and for the experimental groups 30 zebrafish was treated in each well. The bovine spleen peptide powder dissolved in water was separately administered at a concentration as shown in Table 4 below. Meanwhile, a normal control group (fed in a conventional manner) was set, with a capacity of 3 mL per well. After a 24-hour treatment at 28° C., the MTC in normal zebrafish was tested for the bovine spleen peptide powder.

2.2 Evaluation of the Efficacy in Improving Sleep

The 5 dpf wild type zebrafish of line AB were randomly selected and placed in a 6-well plate, and for the experimental groups 30 zebrafish were treated in each well. The bovine spleen peptide powder dissolved in water was separately administered at a concentration as shown in Table 5 below. The positive control melatonin was in a concentration of 125 μg/mL. Meanwhile, the normal control group (fed in a conventional manner) and the model control group (i.e., the zebrafish model of insomnia established by PTZ) were set, with a capacity of 3 mL per well. After a 24-hour treatment at 28° C., 10 zebrafish from each experimental group were randomly selected and transferred to a 96-well plate, with 20 0 μL per 1 zebrafish and 1 zebrafish per well. Except for the normal control group, all the other experimental groups were given aqueous PTZ to establish a zebrafish model of insomnia. Data were collected by the behavior analyzer. The zebrafish were analyzed for amount of wake after sleep onset and time of wake after sleep onset. The bovine spleen peptide powder was evaluated for its efficacy in sleep improvement through statistical analysis results of the above indicators. The statistical results were expressed as "mean±standard deviation". The SPSS 26.0 software was used to perform the statistical analysis, where $p<0.05$ indicated that there was a statistically significant difference.

3. Detection Results 3.1 MTC

The evaluated MTC for the efficacy of the bovine spleen peptide powder in improving sleep was 250 μg/mL, as detailed in Table 4.

TABLE 4

Experimental results of the determination of the efficacy of the bovine spleen peptide powder in improving sleep at various concentrations (n = 30)

| Groups | Concentration (μg/mL) | Number of deaths (case) | Mortality rate (%) | Phenotypes |
|---|---|---|---|---|
| Normal control group | — | 0 | 0 | No obvious abnormality |
| Bovine spleen peptide powder | 125 | 0 | 0 | Similar to the normal control group |
| | 250 | 0 | 0 | Similar to the normal control group |

TABLE 4-continued

Experimental results of the determination of the efficacy of the bovine spleen peptide powder in improving sleep at various concentrations (n = 30)

| Groups | Concentration (μg/mL) | Number of deaths (case) | Mortality rate (%) | Phenotypes |
|---|---|---|---|---|
| | 500 | 17 | 57 | — |
| | 1000 | 30 | 100 | — |
| | 2000 | 30 | 100 | — |

3.2 Evaluation of the Efficacy in Improving Sleep

Figures 6A, 6B:
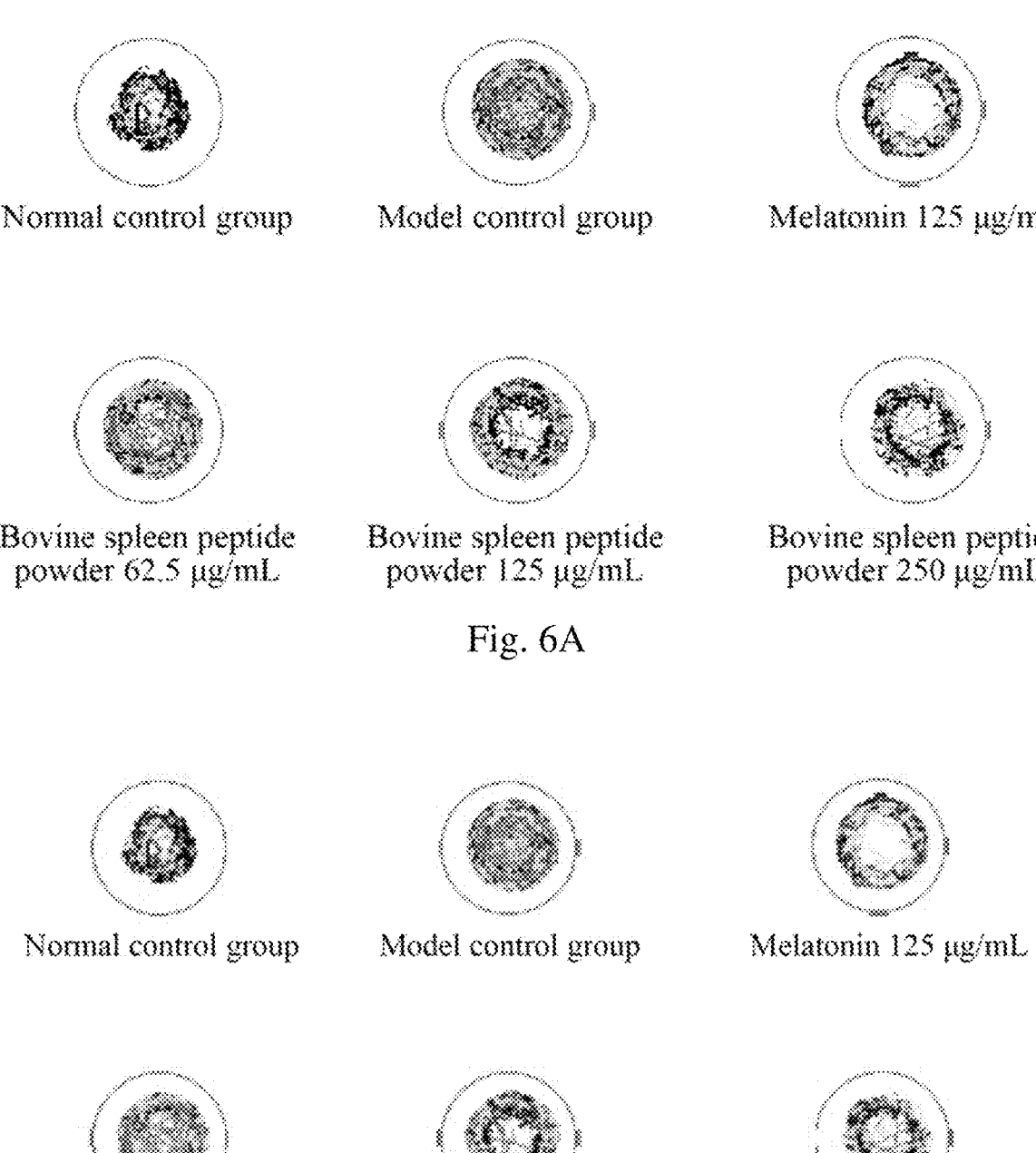
FIGS. 6A-6B show typical diagrams of trajectories of zebrafish after treated with the bovine spleen peptide powder. The black lines in A correspond to the black lines in B, and represent the distance of slow-speed movements. The green lines in A correspond to the light gray lines in B, and represent the distance of medium-speed movements. The red lines in A correspond to the dark gray lines in B, and represent the distance of high-speed movements.
Figure 7:
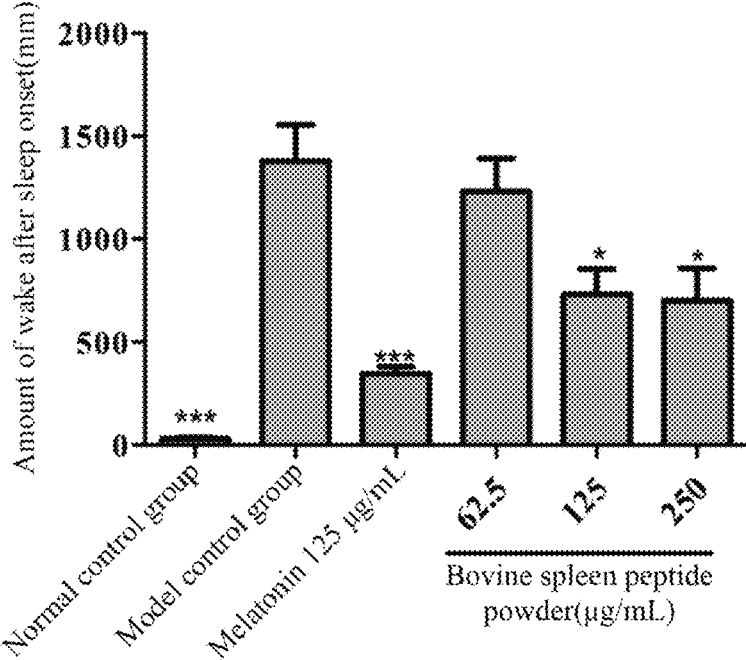
FIG. 7 shows a diagram of the amount of wake after sleep onset of zebrafish after treated with the bovine spleen peptide powder, where * represents p<0.05 and *** represents p<0.001, as compared to the model control group.
Figure 8:
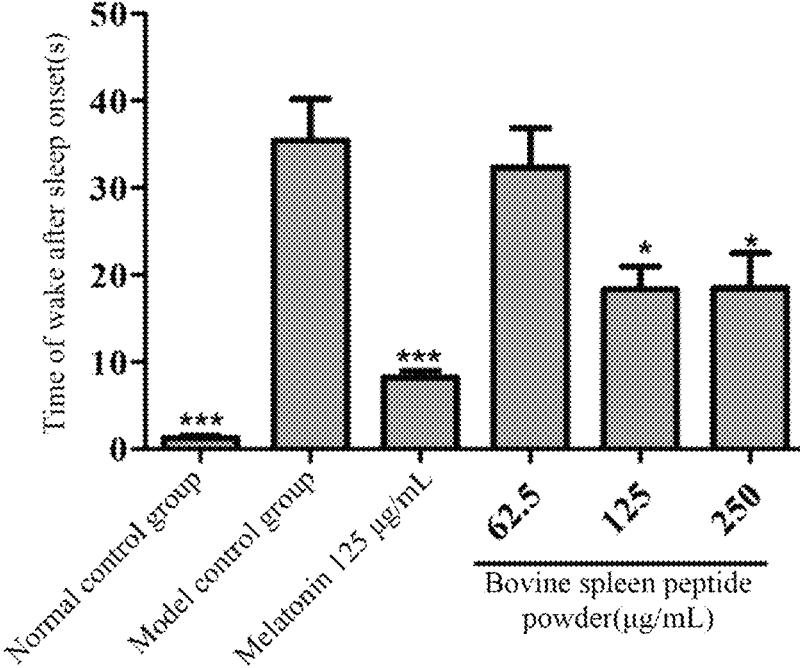
FIG. 8 shows a diagram of the amount of wake after sleep onset of zebrafish after treated with the bovine spleen peptide powder, where * represents p<0.05 and *** represents p<0.001, as compared to the model control group.

The results of Table 5 and FIGS. 6-8 showed that the bovine spleen peptide powder had the efficacy in improving sleep, as evidenced by the decreases in the amount of wake after sleep onset and in the time of wake after sleep onset.

TABLE 5

Experimental results of evaluation of the efficacy of the bovine spleen peptide powder in improving sleep (n = 10)

| Groups | Concentration (μg/mL) | Amount of wake after sleep onset (mm, mean ± standard deviation) | Time of wake after sleep onset (s, mean ± standard deviation) |
|---|---|---|---|
| Normal control group | — | 31.3 ± 6.96*** | 1.27 ± 0.295*** |
| Model control group | — | 1380 ± 176 | 35.5 ± 4.73 |
| Melatonin | 125 | 346 ± 35.3*** | 8.18 ± 0.795*** |
| Bovine spleen peptide powder | 62.5 | 1233 ± 160 | 32.3 ± 4.56 |
| | 125 | 732 ± 121* | 18.4 ± 2.61* |
| | 250 | 702 ± 158* | 18.5 ± 4.04* |

Note:
*represented $p < 0.05$ and
***represented $p < 0.001$, as compared to the model control group.

Example 3 Validation of Antidepressant Efficacy of the Bovine Spleen Peptide Powder 1. Materials for Detection 1.1 Information about Sample Preparation The bovine spleen peptide powder was prepared into a stock solution of 20.0 mg/mL with standard dilution water, sonicated and was ready for use.

Positive control: Zoloft® sertraline hydrochloride tablets (sertraline in short hereinafter), from Pfizer Pharmaceutical Co., Ltd., under catalogue No. DP1626, which was stored in a cool and dry environment. It was prepared with ultrapure water into a stock solution of 5.00 mg/mL, sonicated, centrifuged and stored at −20° C.

1.2 Experimental Animals

The zebrafish, provided by the fish breeding center of Hangzhou Huante Biotechnology Co., Ltd., were all housed in fish water at 28° C. (water quality: 200 mg of instant sea salt per 1 L of reverse osmosis water, with a conductivity of 450-550 μS/cm; a pH of 6.5-8.5; a hardness of 50-100 mg/L $CaCO_3$), and the laboratory animal use license number was SYXK (Zhejiang) 2022-0004. The feeding management fulfilled the requirements of international AAALAC certification (certification number: 001458).

The wild-type zebrafish of AB line were propagated by the way of natural pairwise breeding. Zebrafish aged 5 days post-fertilization (5 dpf) were used for the maximum toleration concentration (MTC) measurement and evaluation of antidepressant efficacy of the bovine spleen peptide powder.

US 12,648,965 B2

17

1.3 Instruments, Consumables and Reagents

A dissecting microscope (SZX7, OLYMPUS, Japan); a CCD camera (VertA1, Shanghai Tusen Vision Technology Co., Ltd., China); a precision electronic balance (CP214, OHAUS, USA); a behavior analyzer (Zebra Lab 3.22.3.31, Viewpoint, France); 6-well plates (Nest Biotech, China); and 24-well plates (Nest Biotech, China).

Reserpine (batch number 11905136, Shanghai Aladdin Biochemical Technology Co., Ltd., China); dimethyl sulfoxide (DMSO, batch BCCD8942, Sigma, Switzerland).

2. Detection Method 2.1 MTC Assay

The 5 dpf wild type zebrafish of line AB were randomly selected and placed in a 6-well plate, and for the experimental groups 30 zebrafish were treated in each well. The bovine spleen peptide powder dissolved in water was separately administered at a concentration as shown in Table 6 below. Meanwhile, the normal control group (fed in a conventional manner) and the model control group (the zebrafish model of clinical depression established by reserpine) were set, with a capacity of 3 ml per well. except for the normal control group, each experimental group was given aqueous reserpine to establish a zebrafish model of clinical depression. after a 24-hour treatment at 28° C., the MTC on model zebrafish was tested for the bovine spleen peptide powder.

2.2 Evaluation of Antidepressant Efficacy

The 5 dpf wild type zebrafish of line AB were randomly selected and placed in a 6-well plate, and for the experimental groups 30 zebrafish were treated in each well. The bovine spleen peptide powder dissolved in water was separately administered at a concentration as shown in Table 7 below. The positive control sertraline was in a concentration of 100 ng/mL. Meanwhile, the normal control group (fed in a conventional manner) and the model control group were set, with a capacity of 3 mL per well. Except for the normal control group, each experimental group was given aqueous reserpine to establish a zebrafish model of clinical depression. After a 24-hour treatment at 28° C., 10 zebrafish from each experimental group were randomly selected and determined for the time ratio of movements in bright field and distance of movement in bright field of zebrafish by the behavior analyzer. Statistical analysis results were used to evaluate the sample for its antidepressant efficacy. The statistical results were expressed as "mean±standard deviation". The SPSS 26.0 software was used to perform the statistical analysis, where p<0.05 indicated that there was a statistically significant difference.

3. Detection Results 3.1 MTC

The evaluated MTC for the antidepressant efficacy of the bovine spleen peptide powder was 250 μg/mL, as detailed in Table 6.

TABLE 6

Experimental results of the determination of antidepressant efficacy at various concentrations (n = 30)

| Groups | Concentration (μg/mL) | Number of deaths (case) | Mortality rate (%) | Phenotypes |
|---|---|---|---|---|
| Normal control group | — | 0 | 0 | No apparent abnormality |
| Model control group | — | 0 | 0 | All attached to wall |

18

TABLE 6-continued

Experimental results of the determination of antidepressant efficacy at various concentrations (n = 30)

| Groups | Concentration (μg/mL) | Number of deaths (case) | Mortality rate (%) | Phenotypes |
|---|---|---|---|---|
| Bovine spleen peptide powder | 125 | 0 | 0 | Similar to the state of the model control group |
| | 250 | 0 | 0 | Similar to the state of the model control group |
| | 500 | 1 | 3 | More severe than model control group |
| | 1000 | 27 | 90 | — |
| | 2000 | 30 | 100 | — |

3.2 Evaluation of Antidepressant Efficacy

Figure 9:
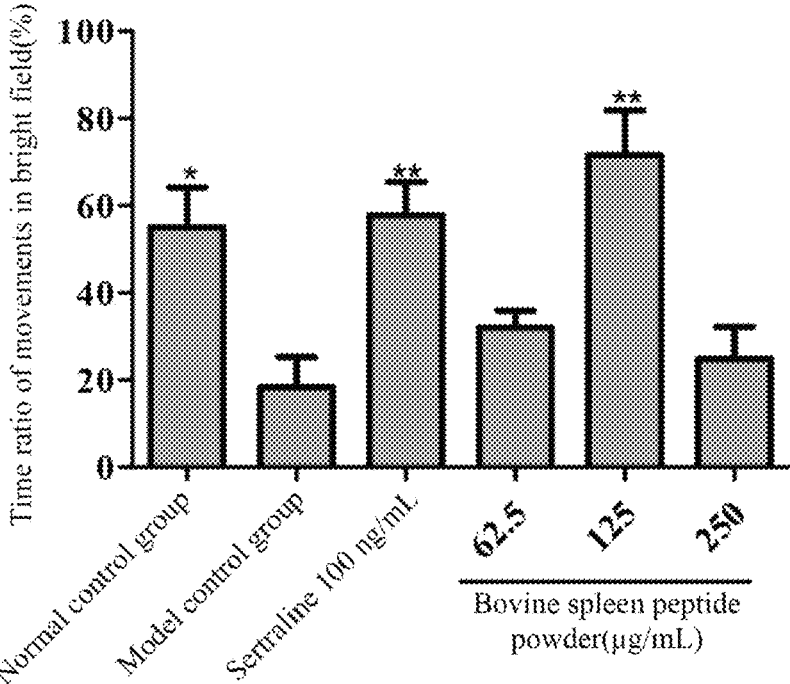
FIG. 9 shows a diagram of the time ratio of zebrafish movements in bright field after treated with the bovine spleen peptide powder, where * represents p<0.05 and ** represents p<0.01, as compared to the model control group.
Figure 10:
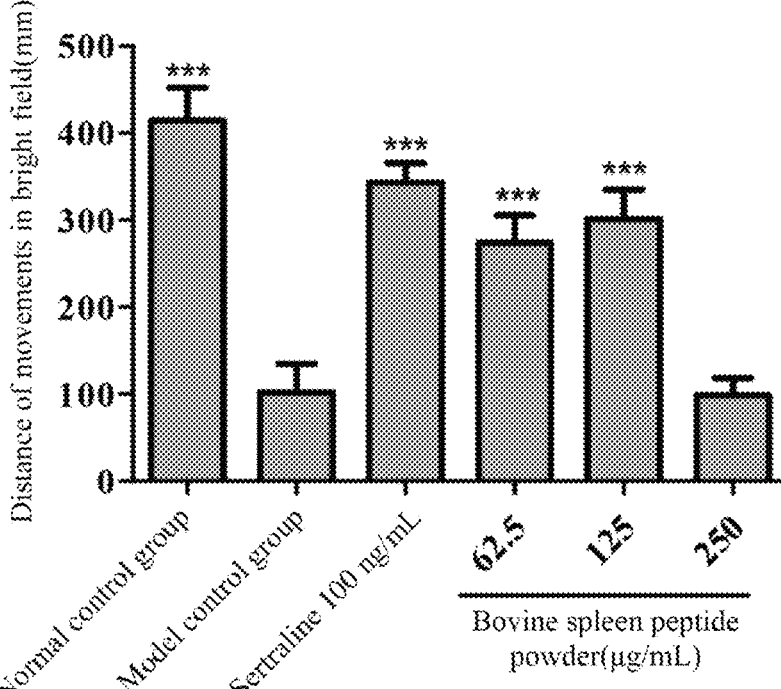
FIG. 10 shows a diagram of the distance of zebrafish movements in bright field after treated with the bovine spleen peptide powder, where *** represents p<0.001, as compared to the model control group.

The results in Table 7 and FIGS. 9-10 showed that compared to the control group of the clinical depression model, zebrafish with the administration of the bovine spleen peptide powder had increased time ratio of movements in bright field and distance of movements in bright field, with the skototaxis state of zebrafish model of clinical depression improved, demonstrating the antidepressant efficacy of the bovine spleen peptide powder.

TABLE 7

Experimental results of antidepressant efficacy (n = 10)

| Groups | Concentration (μg/mL) | Time ratio of movements in bright field (%, mean ± standard deviation) | Distance of movements in bright field (mm, mean ± standard deviation) |
|---|---|---|---|
| Normal control group | — | 55.1 ± 9.05* | 414 ± 37.9*** |
| Model control group | — | 18.4 ± 6.89 | 102 ± 32.9 |
| Sertraline | 100 ng/mL | 57.8 ± 7.64** | 343 ± 22.7*** |
| Bovine spleen peptide powder | 62.5 | 32.1 ± 3.79 | 274 ± 31.9*** |
| | 125 | 71.6 ± 10.2** | 301 ± 33.8*** |
| | 250 | 24.9 ± 7.29 | 98.6 ± 19.4 |

Note:
*represented $p < 0.05$,
**represented $p < 0.01$ and
***represented $p < 0.001$, as compared to model control group.

Example 4 Regulatory Effect of the Bovine Spleen Peptide Powder on Intestinal Goblet Cells 1. Materials for Detection 1.1 Information about Sample Preparation The bovine spleen peptide powder was prepared into a stock solution of 20.0 mg/mL with standard dilution water, sonicated and was ready for use.

Positive control: prednisone, a white powder from Shanghai Macklin Biochemical Technology Co., Ltd., under batch number C10016501, was stored at 4° C. It was prepared with DMSO into a stock solution of 15.0 mg/mL and stored at −20° C.

1.2 Experimental Animals

The zebrafish, provided by the fish breeding center of Hangzhou Huante Biotechnology Co., Ltd., were all housed in fish water at 28° C. (water quality: 200 mg of instant sea salt per 1 L of reverse osmosis water, with a conductivity of 450-550 μS/cm; a pH of 6.5-8.5; a hardness of 50-100 mg/L CaCO₃), and the laboratory animal use license number was SYXK (Zhejiang) 2022-0004. The feeding management fulfilled the requirements of international AAALAC certification (certification number: 001458).

The wild-type zebrafish of AB line were propagated by the way of natural pairwise breeding. Zebrafish aged 3 days post-fertilization (3 dpf) were used for the maximum toleration concentration (MTC) measurement and evaluation of efficacy of the bovine spleen peptide powder for improving intestinal functions.

1.3 Instruments, Consumables and Reagents

A dissecting microscope (SZX7, OLYMPUS, Japan); a CCD camera (VertA1, Shanghai Tusen Vision Technology Co., Ltd., China); a microtome (KD2258, Jinhua Kedi Medical Devices Co., Ltd., China); and 6-well plates (Nest Biotech, China).

Trinitrobenzenesulfonic acid (TNBS, batch No. SLCK4178, Sigma, USA); alcian blue (batch No. BCBV8028, Sigma, Switzerland); dimethyl sulfoxide (DMSO, batch No. BCCD8942, Sigma, Switzerland); glacial acetic acid (batch No. C10323745, Shanghai Macklin Biochemical Technology Co., Ltd., China); methyl cellulose (batch No. G2106167, Shanghai Aladdin Biochemical Technology Co., Ltd., China); 4% tissue and cell fixative solution (batch No. 20210828, Beijing Solarbio Technology Co., Ltd., China); xylene (batch No. 20201113, Sinopharm Chemical Reagent Co., Ltd., China); PBS buffer (batch No. 70115000, Biosharp, China); Mayer hematoxylin staining solution (batch No. 20220120, Shanghai Yihe Biotechnology Co., Ltd., China); eosin staining solution (batch No. 20220120, Shanghai Yihe Biotechnology Co., Ltd., China); Neutral gum (batch No. 330A021, Solarbio, China); Huabao's Paraffin for High Efficiency Section (batch No. 20210828, Shanghai Huayong Paraffin Co., Ltd., China); and anhydrous ethanol (batch No. 20210107, Sinopharm Chemical Reagent Co., Ltd., China).

2. Detection Method 2.1 MTC Assay

The 3 dpf wild type zebrafish of line AB were randomly selected and placed in a 6-well plate, and for the experimental groups 30 zebrafish was treated in each well. Except for the normal control group (fed in a conventional manner), all the other experimental groups were given aqueous TNBS to establish a zebrafish model of gastrointestinal mucosal injury. After a 2-day treatment at 28° C., TNBS was removed, and the bovine spleen peptide powder dissolved in water was given at a concentration as shown in Table 8 below. Meanwhile, a normal control group and a model control group were set, with a capacity of 3 mL per well. After a 2-day treatment at 28° C., the MTC in the zebrafish model of gastrointestinal mucosal injury was tested for the bovine spleen peptide powder.

2.2 Evaluation of Regulatory Efficacy on Intestinal Goblet Cells

The 3 dpf wild type zebrafish of line AB were randomly selected and placed in a 6-well plate, and for the experimental groups 30 zebrafish were treated in each well. Except for the normal control group (fed in a conventional manner), all the other experimental groups were given aqueous TNBS to establish a zebrafish model of gastrointestinal mucosal injury. After a 2-day treatment at 28° C., TNBS was removed, and the bovine spleen peptide powder dissolved in water was given at a concentration as shown in Table 9 below. The positive control prednisone was at a concentration of 15.0 μg/mL. Meanwhile, a normal control group and a model control group (i.e., a zebrafish model of gastrointestinal mucosal injury model established by TNBS) were set, with a capacity of 3 mL per well. After a further 2-day treatment at 28° C., 10 zebrafish from each experimental group were randomly selected and placed under the dissecting microscope for photographing. Data were acquired by the NIS-Elements D 3.20 advanced image processing software. The number of goblet cells in the intestine of zebrafish was analyzed. Statistical results were used to evaluate the regulatory efficacy of the goblet cells in the intestine of the zebrafish. The statistical results were expressed as "mean±standard deviation". The SPSS 26.0 software was used to perform the statistical analysis, where $p<0.05$ indicated that there was a statistically significant difference.

3. Detection Results 3.1 MTC

The MTC of the bovine spleen peptide powder for the efficacy in regulating goblet cells was 250 μg/mL, as detailed in Table 8.

TABLE 8

Experimental results of the determination of the efficacy of the bovine spleen peptide powder in regulating goblet cells (n = 30)

| Groups | Concentration (μg/mL) | Number of deaths (case) | Mortality rate (%) | Phenotypes |
|---|---|---|---|---|
| Normal control group | — | 0 | 0 | No apparent abnormality |
| Model control group | — | 0 | 0 | No apparent abnormality |
| Bovine spleen peptide powder | 125 | 0 | 0 | Similar to the state of the model control group |
| | 250 | 0 | 0 | Similar to the state of the model control group |
| | 500 | 30 | 100 | — |
| | 1000 | 30 | 100 | — |

Figure 11:
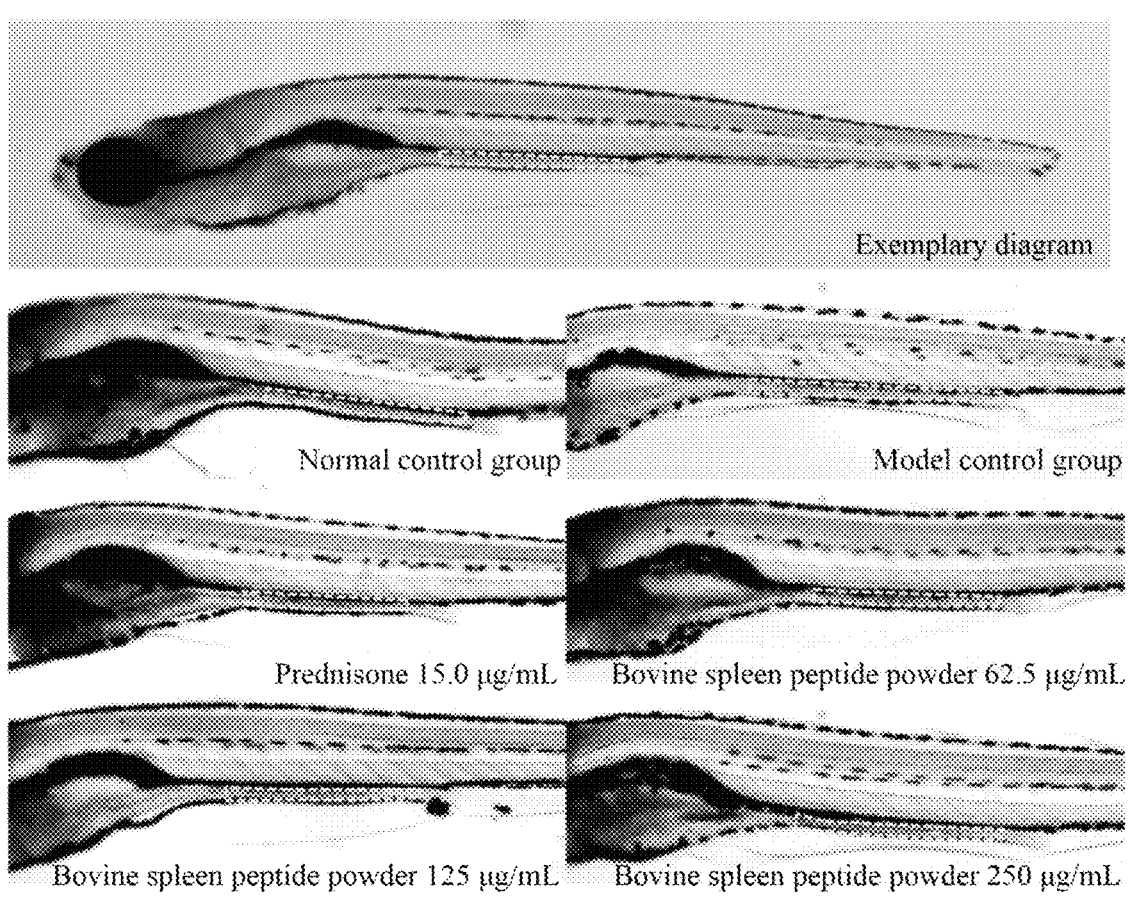
FIG. 11 shows a typical diagram of the number of intestinal goblet cells in zebrafish after treated with the bovine spleen peptide powder, where the dashed lines are the gut within the analysis area and the particles are goblet cells.
Figure 12:
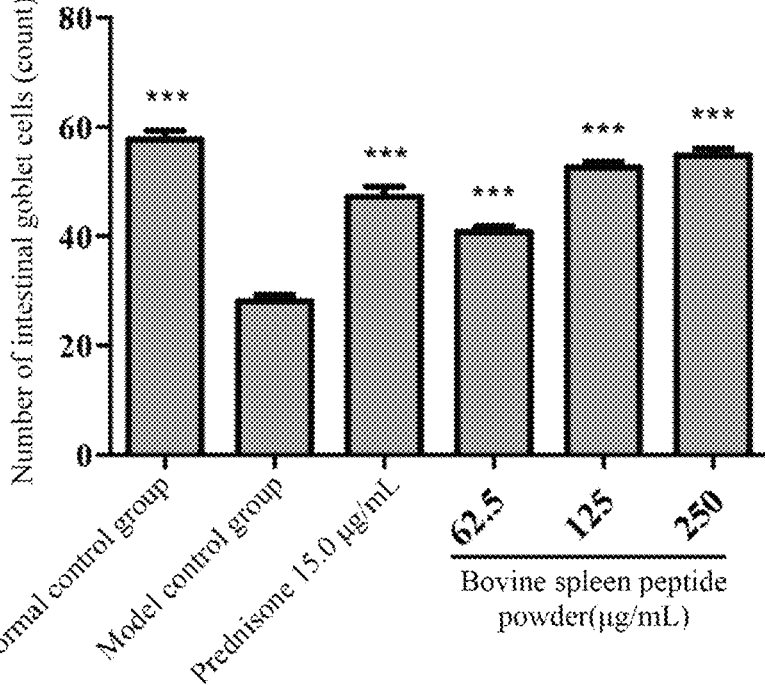
FIG. 12 shows a diagram of the number of intestinal goblet cells after treated with the bovine spleen peptide powder, where *** represents p<0.001, as compared to the model control group.

3.2 Regulatory Efficacy of the Bovine Spleen Peptide Powder on Intestinal Goblet Cells The results in Table 9 and FIGS. 11-12 showed that the bovine spleen peptide powder had a regulatory efficacy on goblet cells and was capable of increasing the number of intestinal goblet cells.

TABLE 9

Experimental results of the evaluation of the regulatory efficacy of the bovine spleen peptide powder on intestinal goblet cells (n = 10)

| Groups | Concentration (μg/mL) | Number of intestinal goblet cells (count, mean ± standard deviation) |
|---|---|---|
| Normal control group | — | 57.7 ± 1.67*** |
| Model control group | — | 28.1 ± 1.22 |
| Prednisone | 15.0 | 47.2 ± 1.89*** |
| Bovine spleen peptide powder | 62.5 | 40.8 ± 1.02*** |
| | 125 | 52.6 ± 1.05*** |
| | 250 | 54.8 ± 1.20*** |

Note:
***represented $p < 0.001$ as compared to the model control group.

Example 5 Evaluation of the Efficacy of the Bovine Spleen Peptide Powder in Preventing Constipation 1. Materials for Detection 1.1 Information about Sample Preparation The bovine spleen peptide powder was prepared into a stock solution of 20.0 mg/mL with standard dilution water, sonicated and was ready for use.

Positive control: spirulina-alfalfa powder, which was a white powder from Perfect (China) Co., Ltd., under batch No. 145611, and stored in a cool environment. It was prepared with standard dilution water into a stock solution of 2.00 mg/mL and was ready for use.

1.2 Experimental Animals

The zebrafish, provided by the fish breeding center of Hangzhou Huante Biotechnology Co., Ltd., were all housed in fish water at 28° C. (water quality: 200 mg of instant sea salt per 1 L of reverse osmosis water, with a conductivity of 450-550 μS/cm; a pH of 6.5-8.5; a hardness of 50-100 mg/L CaCO₃), and the laboratory animal use license number was SYXK (Zhejiang) 2022-0004. The feeding management fulfilled the requirements of international AAALAC certification (certification number: 001458).

The wild-type zebrafish of AB line were propagated by the way of natural pairwise breeding. Zebrafish aged 5 days post-fertilization (5 dpf) were used for the maximum toleration concentration (MTC) measurement and evaluation of efficacy of the bovine spleen peptide powder in preventing constipation.

1.3 Instruments, Consumables and Reagents

A dissecting microscope (SZX7, OLYMPUS, Japan); a CCD camera (VertA1, Shanghai Tusen Vision Technology Co., Ltd., China); a continuous zoom fluorescence microscope with electric focusing (AZ100, Nikon, Japan); a precision electronic balance (CP214, OHAUS, USA); and 6-well plate (Nest Biotech, China).

Methyl cellulose (batch No. C2004046, Shanghai Aladdin Biochemical Technology Co., Ltd., China); aluminum sulfate (batch No. D1909026, Shanghai Aladdin Biochemical Technology Co., Ltd., China); and Nile red (batch No. SLBP9326V, Sigma, India).

2. Detection Method 2.1 MTC Assay

The 5 dpf wild type zebrafish of line AB were randomly selected and placed in a 6-well plate, and for the experimental groups 30 zebrafish was treated in each well. The bovine spleen peptide powder dissolved in water was given at the concentrations as shown in Table 10 below. Meanwhile, a normal control group (fed in a conventional manner) and a model control group (a model of constipation established by aluminum sulfate) were set, with a capacity of 3 mL per well. After a 2-day treatment at 28° C., the bovine spleen peptide powder was removed, and aqueous Neil red was given to each experimental group for staining gastrointestinal tract. At the end of the staining, except for the normal control group, all the other experimental groups were given aqueous aluminum sulfate to establish a model of constipation. After treatment with aluminum sulfate for 6 h, the MTC on the zebrafish model was tested for the bovine spleen peptide powder.

2.2 Evaluation of Efficacy of Constipation Prevention

The 5 dpf wild type zebrafish of line AB were randomly selected and placed in a 6-well plate, and for the experimental groups 30 zebrafish were treated in each well. The bovine spleen peptide powder dissolved in water was given at the concentrations as shown in Table 11 below. The positive control spirulina-alfalfa powder was at a concentration of 667 μg/mL. Meanwhile, a normal control group (fed in a conventional manner) and a model control group (a model of constipation established by aluminum sulfate) were set, with a capacity of 3 mL per well. After a 24-hour treatment at 28° C., the bovine spleen peptide powder was removed, and aqueous Neil red was given to each experimental group for staining gastrointestinal tract. At the end of the staining, except for the normal control group, all the other experimental groups were given aqueous aluminum sulfate to establish a model of constipation.

After treatment with aluminum sulfate for 6 h, 10 zebrafish from each experimental group were randomly selected and placed under the dissecting microscope for photographing, and images were saved. Data were acquired by the NIS-Elements D 3.20 advanced image processing software. The fluorescence intensity in gastrointestinal tract of zebrafish was analyzed. Statistical results were used to evaluate the efficacy of the bovine spleen peptide powder in preventing constipation. The statistical results were expressed as "mean±standard deviation". The SPSS 26.0 software was used to perform the statistical analysis, where $p<0.05$ indicated that there was a statistically significant difference.

3. Detection Results 3.1 MTC

The MTC of the bovine spleen peptide powder for the efficacy in preventing constipation was 250 μg/mL, as detailed in Table 10.

TABLE 10

Experimental results of the determination of the efficacy of the bovine spleen peptide powder in preventing constipation in various concentrations (n = 30)

| Groups | Concentration (μg/mL) | Number of deaths (case) | Mortality rate (%) | Phenotypes |
|---|---|---|---|---|
| Normal control group | — | 0 | 0 | No apparent abnormality |
| Model control group | — | 0 | 0 | No obvious abnormality |
| Bovine spleen peptide powder | 125 | 0 | 0 | Similar to the state of the model control group |
| | 250 | 0 | 0 | Similar to the state of the model control group |
| | 500 | 30 | 100 | — |
| | 1000 | 30 | 100 | — |

3.2. Evaluation of Efficacy in Preventing Constipation

Figure 13:
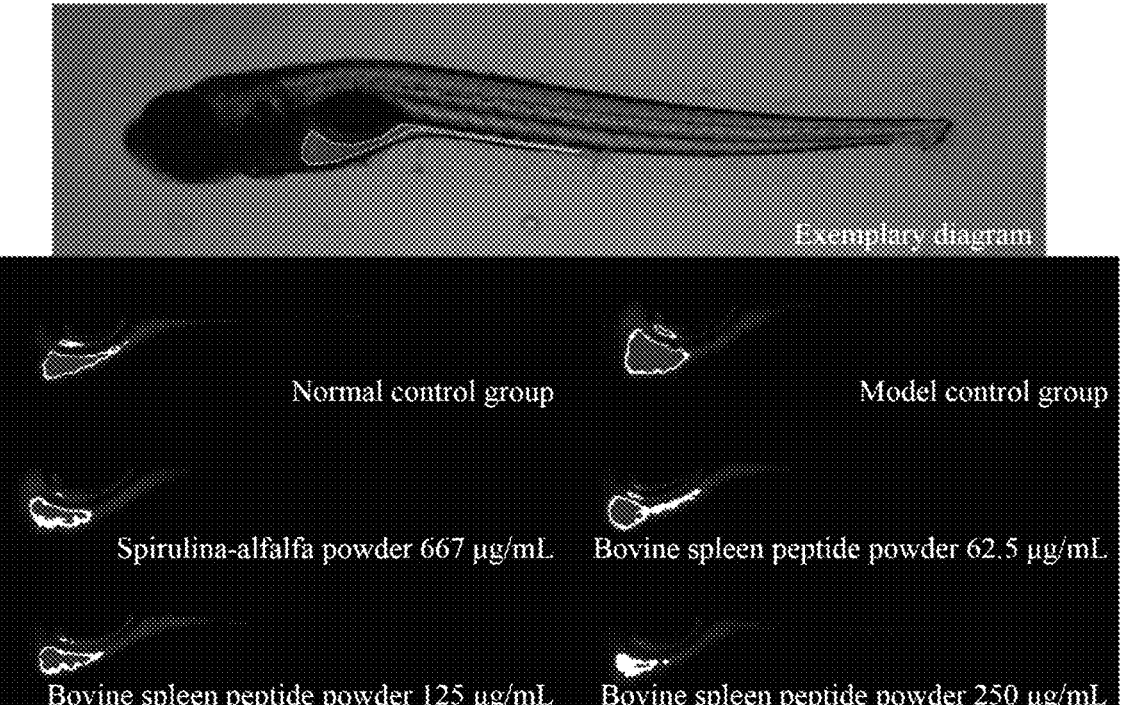
FIG. 13 shows a typical diagram of the gastrointestinal fluorescence intensity in zebrafish after treated with the bovine spleen peptide powder, wherein the dashed box in the exemplary graph is the analysis site in gastrointestinal tract of the zebrafish.
Figure 14:
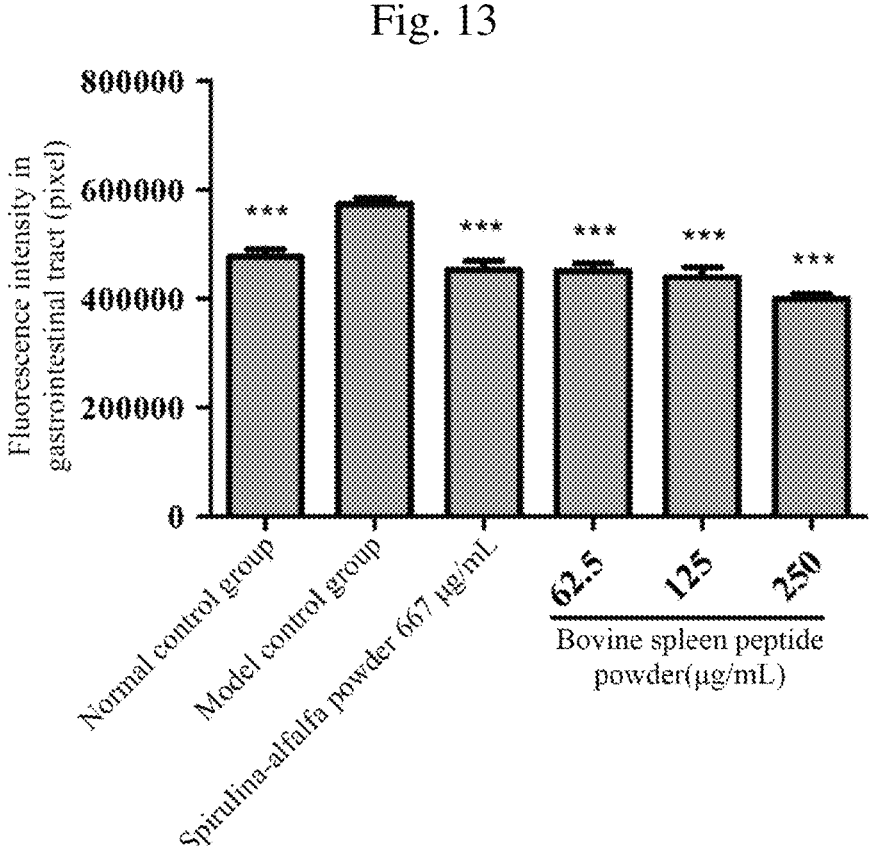
FIG. 14 shows a diagram of the gastrointestinal fluorescence intensity in zebrafish after treated with the bovine spleen peptide powder, where *** represents p<0.001, as compared to the model control group.

The results in Table 11 and FIGS. 13-14 showed that the bovine spleen peptide powder had the efficacy of preventing constipation.

TABLE 11

Experimental results of the evaluation of the efficacy of the bovine spleen peptide powder in preventing constipation (n = 10)

| Groups | Concentration (μg/mL) | Fluorescence intensity in gastrointestinal tract (pixel, mean ± standard deviation) |
|---|---|---|
| Normal control group | — | 476827 ± 14379*** |
| Model control group | — | 573716 ± 10983 |
| Spirulina-alfalfa powder | 667 | 452945 ± 16939*** |
| | 62.5 | 450971 ± 13759*** |
| Bovine spleen peptide powder | 125 | 438738 ± 19056*** |
| | 250 | 399817 ± 8445*** |

Note:
***represented p < 0.001 as compared to the model control group.

All publications and patent documents cited in this specification are incorporated herein by reference to the extent that each individual publication or patent was specifically indicated to be incorporated herein by reference. Various changes and substitutions by equivalents may be made to the embodiments disclosed herein without departing from the true spirit and scope of the disclosure. Unless otherwise indicated above and below, any feature, step, or embodiment of the embodiments of the disclosure may be used in combination with any other feature, step, or embodiment.

What is claimed is:

1. A method of alleviating, or treating clinical depression in a subject comprising administering to the subject an effective amount of bovine spleen peptide powder.

2. The method of claim 1, wherein the bovine spleen peptide powder is used at a concentration of no more than 250 μg/mL.

3. The method of claim 1, wherein the bovine spleen peptide powder is used at a concentration of 62.5-250 μg/mL.

4. The method of claim 1, wherein the bovine spleen peptide powder, or the bovine spleen peptide powder together with food excipients, is prepared into a food product.

5. The method of claim 4, wherein the food product is food for special medical purposes or a health-care food product.

6. The method of claim 4, wherein the food product is a tablet, a powder, a granule, a medicinal tea, a hard capsule, a soft capsule, an oral liquid, a pill, a medicinal wine, an ointment, a beverage, pastry, liquid milks, biscuits, confectionery, a raw material extract or a nutrient premix.

7. The method of claim 1, wherein the bovine spleen peptide powder is formulated with a pharmaceutically acceptable carrier into a pharmaceutically acceptable dosage form.

8. The method of claim 7, wherein the pharmaceutically acceptable dosage form is an oral liquid, a capsule, a powder, a tablet, a granule, a pill, a syrup, a suppository or an injection.

9. The method of claim 1, wherein the bovine spleen peptide powder is administered orally, subcutaneously, intramuscularly or intraperitoneally.

10. The method of claim 1, wherein the bovine spleen peptide powder is administered orally.

11. The method of claim 1, wherein the subject is a vertebrate.

12. The method of claim 1, wherein the subject is fish, a mammal, cyclostomata, an amphibian, a reptile or an avian.

13. The method of claim 1, wherein the subject is fish or a mammal.

14. The method of claim 1, wherein the subject is a zebrafish or humans.

15. The method of claim 1, wherein the bovine spleen peptide powder is prepared by a process comprising the following steps:

fragmentizing and homogenizing a bovine spleen to obtain a spleen slurry;

freezing and thawing the spleen slurry;

performing solid-liquid separation on the frozen and thawed spleen slurry to collect a supernatant;

filtering the supernatant to obtain a bovine spleen extract;

sterilizing the bovine spleen extract; and drying the sterilized bovine spleen extract to obtain the bovine spleen peptide powder.

16. The method of claim 1, wherein polypeptides in the bovine spleen peptide powder are present in an amount of 195.8 mg/g.

17. The method of claim 1, wherein polypeptide molecules in the bovine spleen peptide powder have molecular weights of less than 17 KD.

18. The method of claim 1, wherein amino acids in the bovine spleen peptide powder are present in an amount of 444.5 mg/g.

* * * * *